United States Patent [19]

Robertson

[11] Patent Number: 4,629,740

[45] Date of Patent: Dec. 16, 1986

[54] ANTICONVULSANT AGENTS

[75] Inventor: David W. Robertson, Indianapolis, Ind.

[73] Assignee: Eli Lilly and Company, Indianapolis, Ind.

[21] Appl. No.: 598,569

[22] Filed: Apr. 10, 1984

[51] Int. Cl.$^4$ .................. A61K 31/165; C07C 103/22; C07C 103/28
[52] U.S. Cl. .................................. 514/620; 564/166; 564/168

[58] Field of Search ................ 424/324; 564/168, 166; 514/620

[56] References Cited

U.S. PATENT DOCUMENTS 4,379,165  4/1983  Clark ................................... 424/324

Primary Examiner—Stanley J. Friedman
Attorney, Agent, or Firm—Robert A. Conrad

[57] ABSTRACT

This invention provides for certain benzamide derivatives and their pharmaceutical formulations and their use as anticonvulsant agents.

9 Claims, No Drawings

ANTICONVULSANT AGENTS

BACKGROUND OF THE INVENTION

The several anticonvulsant drugs marketed in the United States provide significant seizure relief for only 50-75% of epileptic patients. The therapeutic effects are sometimes accompanied by serious side effects such as sedation, ataxia, psychoses, suicidal depression, gastrointestinal disturbances, gingival hyperplasia, lymphadenopathies, megaloblastic anemias, hepatotoxicity, nephropathies, hirsutism, and fetal malformations. These side effects, which range in severity from mild sedation to death from aplastic anemia, are particularly troublesome since most of the marketed anticonvulsants have very low therapeutic ratios. For example, phenytoin, one of the most widely used anticonvulsants, controls seizures in man only when plasma levels reach 10 mcg./ml. Toxic effects such as nystagmus are seen at around 20 mcg./ml., ataxia is obvious at 30 mcg./ml., and lethargy is apparent at about 40 mcg./ml. See "The Pharmacological Basis of Therapeutics" (Gilman, Goodman, and Gilman, ed., 6th Ed., MacMillan Publishing Co., Inc., New York, N.Y. (1980)), p. 455. In view of these facts, most epileptologists indicate there is a definite need for more selective and less toxic anticonvulsant drugs.

U.S. Pat. No. 4,379,165 claims a method of treating epilepsy and other convulsive disorders by administering certain N-substituted amino-benzamide derivatives. One particularly preferred compound taught in this patent is 4-amino-N-(α-methylbenzyl)benzamide, also known as 4-amino-N-(1-phenylethyl)benzamide. The compound is reported to have a protective index (P.I.) of 9.48, which is the ratio of the $TD_{50}$ (the toxic dose in 50% of the subjects according to the Rotorod toxicity test) to the $ED_{50}$ in the maximal electroshock seizure test (i.e., the effective dose required to abolish the hindlimb tonic-extensor component in 50% of the animals). The patent only discloses and refers to the compound in its racemic form and does not disclose or infer that the compound can exist as separate enantiomers.

SUMMARY OF THE INVENTION

This invention provides for the individual (S)- and (R)-enantiomers of 4-amino-N-(1-phenylethyl)benzamide and pharmaceutically acceptable salts thereof. I have made the surprising discovery that each of the individual enantiomers has a protective index considerably greater than that of the racemate, and that each of the enantiomers alone is less toxic than the racemate.

In addition to the compounds, this invention also provides a method for treating and preventing convulsions in mammals in need of such treatment which comprises administering to said mammal an effective amount of either (R)- or (S)-4-amino-N-(1-phenylethyl)-benzamide or a pharmaceutically acceptable salt thereof.

According to a further aspect of the present invention, there is provided a pharmaceutical formulation which comprises as active ingredient either (R)- or (S)-amino-N-(1-phenylethyl)benzamide or a pharmaceutically acceptable salt thereof in association with a pharmaceutically acceptable carrier or diluent.

DETAILED DESCRIPTION AND PREFERRED EMBODIMENT

The present invention relates to organic compounds that are useful for treating and preventing convulsions in mammals.

Although the (S)-isomer is more potent as an anticonvulsant agent than either the (R)-isomer or the racemate, the (R)-isomer is preferred because of the increased protective index ratio.

The pharmaceutically acceptable acid addition salts of this invention can be prepared by standard methods known in the art employing those acids of sufficient acidity to form acid addition salts with the weakly basic aniline group. These include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, etc. Such pharmaceutically acceptable salts thus include sulfate, metaphosphate, pyrophosphate, chloride, bromide, iodide, fluoride, oxalate, maleate, benzenesulfonate, toluenesulfonate, chlorobenzenesulfonate, methanesulfonate, propanesulfonate, naphthalene-1-sulfonate, naphthalene-2-sulfonate and the like salts. The preferred salts of this invention are those derived from inorganic acids, especially hydrochloric acid.

The compounds of this invention may be prepared from the racemate as taught in U.S. Pat. No. 4,379,165 by standard methods of isomeric resolution known in the art, such as crystallization, salt formation, high pressure liquid chromatography, etc. In addition, the compounds can be prepared by resolving the intermediate nitro derivative in the same manner and then hydrogenating the individual isomers in the usual way.

However, the preferred method of preparing the compounds of this invention employs the identical reaction scheme as taught in the above U.S. patent employing the enantiomerically pure α-methylbenzylamine, both isomers of which are commercially available. Thus, following the general procedure of reaction A in the above patent, the appropriate isomer of α-methylbenzylamine and 4-nitrobenzoyl chloride are reacted in a nonreactive solvent, such as tetrahydrofuran, preferably in the presence of an acid scavenger, such as potassium carbonate. Although it is preferred that the reactants be added in molar ratios of about 1.5:1.0 (4-nitrobenzoyl chloride/α-methylbenzylamine), other molar ratios are completely operative. The reaction is carried out from about room temperature up to the reflux temperature of the reaction mixture. Under the preferred conditions of reflux, the reaction is generally complete in less than 12 hours.

The hydrogenation procedure may be identical with or equivalent to the conditions taught in the U.S. Pat. No. 4,379,165, Reaction B. Generally, the nitro intermediate is hydrogenated under low pressure in a nonreactive solvent such as an alcohol, in the presence of a catalyst, such as palladium on charcoal. The reaction is generally complete in about 2-4 hours.

The compounds of this invention are anticonvulsant agents and may be administered by various routes including the oral, rectal, transdermal, subcutaneous, intravenous, intramuscular, or intranasal routes, being usually employed in the form of a pharmaceutical composition. It is a special feature of these compounds that they are effective following oral administration. Such compositions are prepared in a manner well known in the pharmaceutical art and comprise at least one active compound. Accordingly, the invention includes a pharmaceutical composition comprising as active ingredient (R)- or (S)-4-amino-N-(1-phenylethyl)benzamide or a pharmaceutically acceptable acid addition salt thereof associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The compositions are preferably formulated in a unit dosage form, each dosage containing from about 5 to 500 mg., more usually 25 to 300 mg., of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg./kg. of body weight. In the treatment of adult humans, the range of about 1 to 50 mg./kg., in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following preparations and examples further illustrate the preparation of the intermediates, compounds, and formulations of this invention. The examples are illustrative only and are not intended to limit the scope of the invention in any way.

EXAMPLE 1

A. Preparation of nitro intermediates

Following the procedure entitled "Reaction A" of U.S. Pat. No. 4,379,165, the following nitro intermediates were prepared using either racemic or enantiomerically pure α-methylbenzylamine.

(R,S)-4-nitro-N-(1-phenylethyl)benzamide, yellow flocculent crystals, 73% yield, m.p. 116.5°–118° C.

Analysis: $C_{15}H_{14}N_2O_3$: Calc.: C, 66.66; H, 5.22; N, 10.36. Found: C, 66.62; H, 5.19; N, 10.40.

(S)-4-nitro-N-(1-phenylethyl)benzamide, yellow flocculent crystals, 84% yield, m.p. 136°–137.5° C., $[\alpha]_D^{25} = +37.7°$ (methanol).

Analysis: $C_{15}H_{14}N_2O_3$: Calc.: C, 66.66; H, 5.22; N, 10.36. Found: C, 66.86; H, 5.11; N, 10.42.

(R)-4-nitro-N-(1-phenylethyl)benzamide, yellow flocculent crystals, 78% yield, m.p. 136°–137.5° C., $[\alpha]_D^{25} = -36.7°$ (methanol).

Analysis: $C_{15}H_{14}N_2O_3$: Calc. C, 66.66; H, 5.22; N, 10.36. Found: C, 66.57; H, 5.42; N, 10.17.

B. Reduction of the nitro intermediates

Following the procedure entitled "Reaction B" of U.S. Pat. No. 4,379,165, the following compounds were prepared from the corresponding nitro intermediates.

(R,S)-4-amino-N-(1-phenylethyl)benzamide, white crystals, 88% yield, m.p. 154°–155.5° C.

Analysis: $C_{15}H_{16}N_2O$: Calc.: C, 74.94; H, 6.71; N, 11.66. Found: C, 74.94; H, 6.91; N, 11.42.

(S)-4-amino-N-(1-phenylethyl)benzamide, white crystals, 90% yield, m.p. 185°–186.5° C., $[\alpha]_D^{25} = +96.2°$ (methanol).

Analysis: $C_{15}H_{16}N_2O$: Calc.: C, 74.97; H, 6.71; N, 11.66. Found C, 74.80; H, 6.98; N, 11.43.

(R)-4-amino-N-(1-phenylethyl)benzamide, white crystals, 85% yield, m.p. 185°–187° C., $[\alpha]_D^{25} = -96.3°$ (methanol).

Analysis: $C_{15}H_{16}N_2O$: Calc.: C, 74.97; H, 6.71; N, 11.66. Found: C, 74.73; H, 6.82; N, 11.40.

The following formulation examples may employ as active compounds either of the pharmaceutical compounds of the invention or their pharmaceutically acceptable salts.

EXAMPLE 2

Hard gelatin capsules are prepared using the following ingredients:

|  | Quantity (mg./capsule) |
| --- | --- |
| Active compound | 250 |
| Starch dried | 200 |
| Magnesium stearate | 10 |

The above ingredients are mixed and filled into hard gelatin capsules in 460 mg. quantities.

EXAMPLE 3

A tablet formula is prepared using the ingredients below:

|  | Quantity (mg./tablet) |
| --- | --- |
| Active compound | 250 |
| Cellulose, microcrystalline | 400 |
| Silicon dioxide, fumed | 10 |

-continued

|  | Quantity (mg./tablet) |
| --- | --- |
| Stearic acid | 5 |

The components are blended and compressed to form tablets each weighing 665 mg.

EXAMPLE 4

An aerosol solution is prepared containing the following components:

|  | Weight % |
| --- | --- |
| Active ingredient | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 5

Tablets each containing 60 mg. of active ingredient are made up as follows:

| Active ingredient | 60 mg. |
| --- | --- |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 6

Capsules each containing 80 mg. of medicament are made as follows:

| Active ingredient | 80 mg. |
| --- | --- |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 7

Suppositories each containing 225 mg. of active ingredient are made as follows:

| Active ingredient | 225 mg. |
| --- | --- |
| Saturated fatty acid glycerides to | 2,000 mg. |

The active ingredient is passed through a No. 60 mesh U.S. sieve and suspended in the saturated fatty acid glycerides previously melted using the minimum heat necessary. The mixture is then poured into a suppository mold of nominal 2 g. capacity and allowed to

EXAMPLE 8

Suspensions each containing 50 mg. of medicament per 5 ml. dose are made as follows:

| Active ingredient | 50 mg. |
| --- | --- |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

The compounds of this invention are anticonvulsant agents with a high therapeutic ratio and long half-life and are therefore useful in the treatment and/or prevention of convulsions in mammals. In particular, the compounds are effective against tonic extensor seizures elicited by maximal electroshock and should therefore be useful for treating generalized tonic-clonic ("grand mal"), cortical focal, complex partial (temporal lobe epilepsy), simple partial (focal motor), and post-traumatic seizures in humans. This activity is demonstrated in the electroshock induced convulsion inhibition assay which follows.

In the electroshock induced convulsion inhibition assay (E.S.), the compound to be tested was dissolved in water (5%—sufficient hydrochloric acid was added for those compounds which were not isolated as a salt in order to effect dissolution) and administered by gavage to each of three Cox standard strain albino male mice (18-24 g.) at the dose level being investigated. Sixty minutes after compound administration, the mice were subjected to a 0.1 second, 50 milliampere electroshock through corneal electrodes. The animals were examined and evaluated immediately after the electroshock for the occurrence of clonic, flexor tonic, or extensor tonic convulsions, or death and the $ED_{50}$ was determined for each compound as the dose which inhibited the occurrence of extensor tonic convulsions in one half of the animals immediately after the electroshock. For comparison, 18 milliamperes was usually sufficient to produce extensor tonic convulsions in about half of the control animals; at 50 milliamperes, almost all control animals (receiving vehicle only) died. The test results are summarized in Table I.

The compounds were also evaluated for determining toxic potential. In determining toxic potential as manifested by neurological deficit, ataxia, or sedation, the "horizontal screen" (H.S.) was employed. This test is well accepted as a measure of impaired motor function in mice. The methodology was identical to that taught by Coughenour, et al., *Pharmacology, Biochemistry and Behavior*, 6, 351 (1977). For each compound, the $ED_{50}$ was determined as the dose which caused one half of the animals to fail to reach the top of the screen. The compounds were administered to the mice in the same manner as described above for the electroshock assay 60 minutes before they were tested in the horizontal screen assay. The test results are summarized in Table I.

From the above two test systems, the protective index (P.I.) can be calculated as the ratio of the horizontal screen $ED_{50}$ over the $ED_{50}$ of the electroshock assay. Thus, a large P.I. is indicative of a broader therapeutic range. A large P.I. thus provides a wide margin of safety allowing greater flexibility in treating epilepsy and other convulsive disorders.

As is apparent from the data as summarized in Table I, both of the individual enantiomers are less toxic than the racemate, as determined by the H.S. $ED_{50}$, and both compounds surprisingly give a significantly increased P.I. as compared to the racemate.

TABLE I

Anti-convulsant Activity and side effects of the isomers of 4-Amino-N—(1-phenylethyl)benzamide*

| Isomer | Electroshock $ED_{50}$ (mg./kg.) | Horizontal Screen $ED_{50}$ (mg./kg.) | Protective Index (H.S. $ED_{50}$/E.S. $ED_{50}$) |
| --- | --- | --- | --- |
| (R,S) (racemate) | 12.5 | 105 | 8.4 |
| (S) | 10.0 | 141 | 14.1 |
| (R) | 17.8 | 480 | 27.0 |

*See text for methodology.

I claim:
1. A compound selected from (R)-4-amino-N-(1-phenylethyl)benzamide and (S)-4-amino-N-(1-phenylethyl)-benzamide or a pharmaceutically acceptable salt thereof.
2. The compound of claim 1 which is (R)-4-amino-N-(1-phenylethyl)benzamide or a pharmaceutically acceptable salt thereof.
3. The compound of claim 1 which is (S)-4amino-N-(1-phenylethyl)benzamide or a pharmaceutically acceptable salt thereof.
4. A method for treating or preventing convulsions in mammals in need of such treatment which comprises administering to said mammal an effective amount of a compound of claim 1.
5. The method of claim 4 wherein the compound is (R)-4-amino-N-(1-phenylethyl)benzamide or a pharmaceutically acceptable salt thereof.
6. The method of claim 4 wherein the compound is (S)-4-amino-N-(1-phenylethyl)benzamide or a pharmaceutically acceptable salt thereof.
7. A pharmaceutical formulation useful for the treatment or prevention of convulsions in mammals which comprises an effective amount of a compound of claim 1 in association with a pharmaceutically acceptable carrier or diluent.
8. A formulation of claim 7 wherein the compound is (R)-4-amino-N-(1-phenylethyl)benzamide or a pharmaceutically acceptable salt thereof.
9. A formulation of claim 7 wherein the compound is (S)-4-amino-N-(1-phenylethyl)benzamide or a pharmaceutically acceptable salt thereof.

* * * * *